United States Patent [19]

White et al.

[11] Patent Number: 5,756,294
[45] Date of Patent: May 26, 1998

[54] SUSCEPTIBILITY MUTATION FOR BREAST AND OVARIAN CANCER

[75] Inventors: Marga B. White, Frederick; Lisa K. Sadzewicz, Laurel, both of Md.

[73] Assignee: OncorMed, Inc., Gaithersburg, Md.

[21] Appl. No.: 533,472

[22] Filed: Sep. 25, 1995

[51] Int. Cl.$^6$ .............. C12Q 1/68; C12P 19/34; C07H 21/02; C07H 21/04
[52] U.S. Cl. .............. 435/6; 435/91.2; 536/23.1; 536/24.3; 536/24.33
[58] Field of Search .............. 536/23.1, 24.3–24.33; 435/91.2, 6

[56] References Cited

U.S. PATENT DOCUMENTS

| | | | |
|---|---|---|---|
| 4,401,828 | 8/1983 | Tanger | 530/300 |
| 4,745,060 | 5/1988 | Brown et al. | 435/172.3 |
| 4,879,214 | 11/1989 | Kornher et al. | |
| 4,966,837 | 10/1990 | Brown et al. | |
| 5,002,874 | 3/1991 | Kaufman | 435/69.1 |
| 5,128,129 | 7/1992 | Kit et al. | 424/89 |
| 5,227,289 | 7/1993 | Bradley et al. | |

FOREIGN PATENT DOCUMENTS

| | | | |
|---|---|---|---|
| 95/19369 | 4/1995 | WIPO | C07H 21/02 |

OTHER PUBLICATIONS

Naylor, S. L., et al.: Loss of Heterozygosity of Chromosome 3p Markers in Small–Cell Lung Cancer. Nature 329: 451–454, Oct. 1–7, 1987.

Merajver, S. D., et al.: Somatic Mutations in the BRCA1 gene in Sporadic Ovarian Tumor. Nature Genetics 9: 439–443, Apr. 1995.

Sato, T., et al.: The Human Prohibition Gene Located On Chromosome 17q21 Is Mutated in Sporadic Breast Cancer[1]. Cancer Research 52: 1643–1646, Mar. 16, 1992.

Wooster, R., et al.: Localization of a Breast Cancer Susceptibility Gene, BRCA2, to Chromosome 13q12–13. Science 265: 2088–2089, Sep. 30, 1994.

Boyd, Jeff; : BRCA1: More Than a Hereditary Breast Cancer Gene? Nature Genetics 9: 335–336, Apr. 1995.

Hosking, L., et al.: A Somatic BRCA1 Mutation In An Ovarian Tumor. Nature Genetics 9, 343–344, Apr. 1995.

Simard, J., et al.: Common Origins Of BRCA1 Mutations in Canadian Breast and Ovarian Cancer Families. Nature Genetics 8: 392–398, Dec. 1994.

Shattuck–Eidens, D., et al.: A Collaborative Survey of 80 Mutations in the BRCA1 Breast and Ovarian Cancer Susceptibility Gene. JAMA 273: 535–541, Feb. 15, 1995.

Miki, Y., et al.: A Strong Candidate For the Breast and Ovarian Cancer Susceptibility Gene BRCA1. Science 266: 66–71, Oct. 7, 1994.

Weber, B. L., : Genetic Testing For Breast Cancer. Scientific American Science & Medicine, pp. 12–21, Jan./Feb. 1996 vol. # not relevant.

Easton, D. F., et al.: Breast and Ovarian Cancer Incidence in BRCA1–Mutation Carriers. Am. J. Hum. Genet. 56: 265–271, 1995.

Ford, D., et al.: Risks of Cancer in BRCA1–Mutation Carriers. The Lanchet 343: 692–695, Mar. 19, 1994.

Bishop, D.T.: Genetics of Breast and Ovarian Cancer. The Human Molecular Genetics Series by John K. Cowell, Chapter 5, pp. 93–111, 1995.

Hoskins, K. F., et al.: Assessment and Counseling For Women With A Family History of Breast Cancer. JAMA 273: 577–585, Feb. 15, 1995.

Human Breast and Ovarian Cancer Susceptibility (BRCA1) mRNA, Complete Codes. GenBank Assession No. U14680.
Shattuck–Eidens et al. JAMA 273: 535–541, 1995.
Castilla et al. Nature Genetics 8: 387–391, 1994.
Friedman et al. Nature Genetics 8: 1–6, 1994.
Goldgar et al. J. of Nat. Cancer Inst 86:200–209, 1994.
Futreal et al. Science 266: 120–122, 1994.
Hosking et al. Nature Genetics 9:343–344, 1995.
Simard et al. Nature Genetics 9: 392–398, 1994.
Merajver et al. Nature Genetics 9:439–443, 1995.
Boyd et al. Nature Genetics 9:335–336, 1995.
Sato et al. Cancer Research 52: 1643–1646, 1992.
Wooster et al. Science 265:2088–2090, 1994.
Miki et al. Science 266:66–71, 1994.

*Primary Examiner*—W. Gary Jones
*Assistant Examiner*—Dianne Rees
*Attorney, Agent, or Firm*—Albert P. Halluin; R. Thomas Gallegos; Howrey & Simon

[57] ABSTRACT

A new mutation has been found in the BRCA1 gene. The mutation is a two base pair deletion at nucleotides 3888 and 3889 of the published cDNA sequence of BRCA1 (GENBANK ACCESSION NO:U14680). The invention provides a method for diagnosing persons at risk of developing breast or ovarian cancer. The invention also provides a further tool with which to characterize tumors.

17 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:1:

GCAAAAGCGT CCAGAAAGGA                                                                  20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:2:

AGTCTTCCAA TTCACTGCAC                                                                   20

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:3:

GAACACAGGA GAAT                                                                                        14

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:4:

TAAGAACACA GGAG                                                                                         14

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:5:

GAACACAGAG GAGAA    15

( 2 ) INFORMATION FOR SEQ ID NO:6:

( i ) SEQUENCE CHARACTERISTICS:
  ( A ) LENGTH: 15 base pairs
  ( B ) TYPE: nucleic acid
  ( C ) STRANDEDNESS: Not Relevant
  ( D ) TOPOLOGY: Not Relevant ( i i ) MOLECULE TYPE: DNA (genomic)

( x i ) SEQUENCE DESCRIPTION: SEQ ID NO:6:

TAAGAACACA GAGGA    15

SUSCEPTIBILITY MUTATION FOR BREAST AND OVARIAN CANCER

FIELD OF THE INVENTION

This invention relates to a gene which predisposes individuals to breast and ovarian cancer. More specifically, this invention relates to a specific mutation in the BRCA1 gene. In addition, it also relates to methods for detecting the presence of the mutation.

BACKGROUND OF THE INVENTION

It has been estimated that about 5–10% of breast cancer is inherited Rowell, S., et al., *American Journal of Human Genetics* 55:861–865 (1994). Located on chromosome 17, BRCA1 is the first gene identified conferring increased risk for breast and ovarian cancer. Miki et al., *Science* 266:66–71 (1994). Mutations in this tumor suppressor gene account for roughly 45% of inherited breast cancer and 80–90% of families with increased risk of early onset breast and ovarian cancer. Easton et al., *American Journal of Human Genetics* 52:678–701 (1993).

The location of one or more mutations in the BRCA1 region of chromosome 17 provides a promising approach to reducing the high incidence and mortality associated with breast and ovarian cancer through the early detection of women at high risk. These women, once identified, can be targeted for more aggressive prevention programs. Screening is carried out by a variety of methods which include karyotyping, probe binding and DNA sequencing.

In DNA sequencing technology, genomic DNA is extracted from whole blood and the coding regions of the BRCA1 gene are amplified using the polymerase chain reaction (PCR). Each of the coding regions is sequenced completely and the results are compared to the normal DNA sequence of the gene (GenBank Accession Number U14680 or U15595). Many mutations have already been reported in the BRCA1 gene. Shattuck-Eidens, D., et al., *Journal of the American Medical Association* 273: 535–541 (1995).

The BRCA1 gene (GenBank Accession Number U14680 or U15595) is divided into 24 separate exons. Exons 1 and 4 are noncoding, in that they are not part of the final functional BRCA1 protein product. The BRCA1 coding region spans roughly 5600 base pairs (bp). Each exon consists of 200-400 bp, except for exon 11 which contains about 3600 bp. To sequence the coding region of the BRCA1 gene, each exon is amplified separately and the resulting PCR products are sequenced in the forward and reverse directions. Because exon 11 is so large, we have divided it into twelve overlapping PCR fragments of roughly 350 bp each (segments "A" through "L" of BRCA1 exon 11).

There is a need in the art to identify mutations in the BRCA1 gene. Identification of mutations of the BRCA1 gene and protein would allow more widespread diagnostic screening for hereditary breast and ovarian cancer than is currently possible.

SUMMARY OF THE INVENTION

The present invention is based on the discovery of a two base pair deletion of nucleotides 3888 and 3889 of the published BRCA1 cDNA sequence which is associated with susceptibility to and development of breast and ovarian cancer.

It is an object of the invention to provide a method for determining a predisposition or higher susceptibility to breast and ovarian cancer.

It is another object of the invention to provide a method of characterizing a tumor.

It is another object of the invention to provide primers for detecting and amplifying a region of DNA which contains the 3888delGA mutation.

DETAILED DESCRIPTION OF THE PREFERRED EMBODIMENTS

The present invention is based on the discovery of a two base pair deletion of nucleotides 3888 and 3889 of the published BRCA1 cDNA sequence. This deletion mutation is referred to as 3888delGA. The BRCA1 gene is a tumor suppressor gene associated with breast and ovarian cancer.

The 3888delGA deletion interrupts the normal reading frame of the BRCA1 transcript, resulting in the appearance of an in-frame terminator (TAG) at codon position 1265. This mutation is, therefore, predicted to result in a truncated, and most likely, non-functional protein.

Useful DNA molecules according to the invention are those which will specifically hybridize to BRCA1 sequences in the region of the 3888delGA mutation. Typically these are at least about 20 nucleotides in length and have the nucleotide sequence corresponding to the region of the 3888delGA mutation at nucleotides 3888 and 3889 of the published BRCA1 cDNA sequence (GenBank Accession No.U15595). Such molecules can be labeled, according to any technique known in the art, such as with radiolabels, fluorescent labels, enzymatic labels, sequence tags, etc. According to another aspect of the invention, the DNA molecules contain the 3888delGA mutation. Such molecules can be used as allele-specific oligonucleotide probes to track a particular mutation through a family.

Body samples can be tested to determine whether the BRCA1 gene contains the 3888delGA mutation. Suitable body samples for testing include those comprising DNA, RNA or protein obtained from biopsies, blood, prenatal, or embryonic tissues, for example.

In one embodiment of the invention a pair of isolated oligonucleotide primers are provided.

BRCA1-11K-F: 5'-GCA AAA GCG TCC AGA AAG AG-3'(SEQ ID NO:1), and

BRCA1-11K-R: 5'-AGT CTT CCA ATT CAC TGC AC-3' (SEQ ID NO:2). The designation BRCA1-11K referres to a sequence in the BRCA1 gene, Exon 11, section K. F and R refer to forward and reverse.

The oligonucleotide primers are useful in diagnosis of a subject at risk of having breast or ovarian cancer, and also useful for characterizing a tumor. The primers direct amplification of a target polynucleotide prior to sequencing. These unique BRCA1 exon 11 oligonucleotide primers were designed and produced at OncorMed based upon identification of the 3888delGA mutation.

In another embodiment of the invention a pair of isolated allele specific oligonucleotides are provided.

5'-GAA CAC AGG AGA AT-3'(SEQ ID NO:3), and

5'-TAA GAA CAC AGG AG-3'(SEQ ID NO:4) and sequences substantially similar thereto.

The allele specific oligonucleotides are useful in diagnosis of a subject at risk of having breast or ovarian cancer, and also useful for characterizing a tumor. The allele specifc oligonucleotides hybridize with a target polynucleotide sequence containing the 3888delGA deletion mutation.

The term "substantially complementary to" or "substantially the sequence" refers to (e.g., SEQ ID NO:3 and SEQ ID NO:4) sequences which hybridize to the sequences provided under stringent conditions and/or sequences having sufficient homology with SEQ ID NO:3 and SEQ ID NO:4, such that the allele specific oligonucleotides of the invention hybridize to the sequence. The term "isolated" as used herein includes oligonucleotides substantially free of other nucleic acids, proteins, lipids, carbohydrates or other materials with which they may be associated. Such association being either in cellular material or in a synthesis medium. A "target polynucleotide" refers to the nucleic acid sequence of interest e.g., the BRCA1 encoding polynucleotide. Other primers which can be used for primer hybridization will be known or readily ascertainable to those of skill in the art.

The primers of the invention embrace oligonucleotides of sufficient length and appropriate sequence so as to provide initiation of polymerization on a significant number of nucleic acids in the polymorphic locus. Specifically, the term "primer" as used herein refers to a sequence comprising two or more deoxyribonucleotides or ribonucleotides, preferably more than three, and more preferably more than eight and most preferably at least about 20 nucleotides of the BRCA1 gene wherein said DNA sequence contains the 3888delGA mutation relative to BRCA1 contained in SEQ ID NO's:3 and 4. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859–1862, 1981. One method for synthesizing oligonucleotides on a modified solid support is described in U.S. Pat. No. 4,458,066.

Any nucleic acid specimen, in purified or nonpurified form, can be utilized as the starting nucleic acid or acids, providing it contains, or is suspected of containing, the specific nucleic acid sequence containing the polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in *Molecular Cloning:A Laboratory Manual*, Cold Spring Harbor, N.Y., p 280–281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (e.i., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. PCR, A Practical Approach, ILR Press, Eds. M. J. McPherson, P. Quirke, and G. R. Taylor, 1992.

The amplification products may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et.al., Bio/Technology,3:1008–1012, 1985), allele-specific oligonucleotide (ASO) probe analysis (Conner, et. al., Proc. Natl. Acad. Sci. U.S.A., 80:278, 1983), oligonucleotide ligation assays (OLAs) (Landgren, et. al., Science,241:1007, 1988), and the like. Molecular techniques for DNA analysis have been reviewed (Landgren, et. al., Science, 242:229–237, 1988).

Preferably, the method of amplifying is by PCR, as described herein and as is commonly used by those of ordinary skill in the art. Alternative methods of amplification have been described and can also be employed as long as the BRCA1 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA™) which uses reverse transcription and T7 RNA polymerase and incorporates two primers to target its cycling scheme. NASBA™ amplification can begin with either DNA or RNA and finish with either, and amplifies to $10^8$ copies within 60 to 90 minutes. Alternatively, nucleic acid can be amplified by ligation activated transcription (LAT). Lat works from a single-stranded template with a single primer that is partially single-stranded and partially double-stranded. Amplification is initiated by ligating a cDNA to the promoter olignucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair. Nucleic acid amplification by strand displacement activation (SDA) utilizes a short primer containing a recognition site for hincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling. Another amplification system useful in the method of the invention is the QB Replicase System. Although PCR is the preferred method of amplification if the invention, these other methods can also be used to amplify the BRCA1 locus as described in the method of the invention.

In another embodiment of the invention a method is provided for diagnosing a subject having a predisposition or higher susceptibility to (at risk of) breast or ovarian cancer comprising sequencing a target nucleic acid of a sample from a subject by dideoxy sequencing following amplification of the target nucleic acid.

In another embodiment of the invention a method is provided for diagnosing a subject having a predisposition or higher susceptibility to (at risk of) breast or ovarian cancer comprising contacting a target nucleic acid of a sample from a subject with a reagent that detects the presence of the 3888delGA mutation and detecting the mutation.

In another embodiment of the invention a method is provided for characterizing a tumor. One method comprises sequencing the target nucleic acid isolated from the tumor to determine if the 3888delGA deletion has occured. Sanger, F., et al., J. Mol. Biol. 142:1617 (1980).

Another method comprises contacting a target nucleic acid of a sample from a subject with a reagent that detects the presence of the 3888delGA mutation and detecting the mutation. A number of hybridization methods are well known to those skilled in the art. Many of them are useful in carrying out the invention.

The materials for use in the method of the invention are ideally suited for the preparation of a diagnostic kit. Such a kit may comprise a carrier means being compartmentalized to receive in close confinement one or more container means such as vials, tubes, and the like, each of the container means comprising one of the separate elements to be used in the method. For example, one of the container means may comprise means for amplifying BRCA1 DNA, said means comprising the necessary enzyme(s) and oligonucleotide primers for amplifying said target DNA from the subject. The oligonucleotide primers include primers having a sequence:

5'-GCA AAA GCG TCC AGA AAG AG-3'(SEQ ID NO: 1)

or

5'-AGT CTT CCA ATT CAC TGC AC-3'(SEQ ID NO: 2)

or primer sequences substantially complementary or substantially homologous thereto. The target flanking 5' and 3' polynucleotide sequence has substantially the sequence selected from the group consisting of:

5'-GAA CAC AGG AGA AT-3'(SEQ ID NO: 3), and

5'-TAA GAA CAC AGG AG-3'(SEQ ID NO: 4)

and sequences substantially complementary or homologous thereto. Other oligonucleotide primers for amplifying BRCA1 will be known or readily ascertainable to those of skill in the art.

EXAMPLES

Materials and Methods

Genomic DNA was isolated from white blood cells of a subject with a family history of breast cancer. Dideoxy sequence analysis was performed following polymerase chain reaction amplification of segment K of exon 11.

Exon 11 of the BRCA1 gene was subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo,F., Scanes, C., eds., Academic Press, Inc., 1993. Fluorescent dye was attached for automated sequencing using the TAQ DYE TERMINATOR® sequence terminator Kit (PERKIN-ELMER® cat# 401628). DNA sequencing was performed in both forward and reverse directions on an Applied Biosystems, Inc. (ABI) automated sequencer (Model 377). The software used for analysis of the resulting data was SEQUENCE NAVIGATOR® analytical software purchased through ABI.

Example 1

1. Polymerase Chain Reaction (PCR) Amplification

Genomic DNA (100 nanograms) extracted from white blood cells of the subject was amplified in a final volume of 25 microliters containing 1 microliter (100 nanograms) genomic DNA, 2.5 microliters 10X PCR buffer (100 mM Tris, pH 8.3, 500 mM KCl, 1.2 mM $MgCl_2$), 2.5 microliters 10X dNTP mix (2 mM each nucleotide), 2.5 microliters forward primer (BRCA1-11K-F, 10 micromolar solution), 2.5 microliters reverse primer (BRCA1-11K-R, 10 micromolar solution),and 1 microliter Taq polymerase (5 units), and 13 microliters of water.

The PCR primers used to amplify segment K of exon 11 (where the mutation was found) are as follows:

BRCA1-11K-F: 5'-GCA AAA GCG TCC AGA AAG AG-3' SEQ ID NO: 1

BRCA1-11K-R: 5'-AGT CTT CCA ATT CAC TGC AC-3' SEQ ID NO: 2

The primers were synthesized on an DNA/RNA Synthesizer Model 394®.

Thirty-five cycles were performed, each consisting of denaturing (95° C.; 30 seconds), annealing (55° C.; 1 minute), and extension (72° C.; 90 seconds), except during the first cycle in which the denaturing time was increased to 5 minutes, and during the last cycle in which the extension time was increased to 5 minutes.

PCR products were purified using QIA-QUICK® PCR purification kits (QIAGEN®, cat# 28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye was attached to PCR products for automated sequencing using the TAQ DYE TERMINATOR® sequence terminator Kit (PERKIN-ELMER® cat# 401628). DNA sequencing was performed in both forward and reverse directions on an Applied Biosystems, Inc. (ABI) Foster City, Calif., automated sequencer (Model 377). The software used for analysis of the resulting data was SEQUENCE NAVIGATOR® analytical software purchased through ABI.

3. Detection of the 3888delGA mutation by Allele Specific Oligonucleotide Hybridization For rapid detection of the 3888delGA mutation, unlabeled PCR products from segment K of exon 11 were blotted in duplicate onto a nylon membrane, air dried, and UV crosslinked. Hybridization was accomplished with $^{35}P$ labeled ATP oligonucleotides corresponding to either a normal sequence such as

5'-GAA CAC AGA GGA GAA T-3', (SEQ. ID. NO. 5), or

```
5'-TAA GAA CAC AGA GGA G-3', (SEQ. ID. NO. 6)
``` or with a sequence exhibiting the 3888delGA mutation such as

```
5'-GAA CAC AGG AGA AT-3' (SEQ ID NO: 3), and

5'-TAA GAA CAC AGG AG-3'(SEQ ID NO: 4).
```

The membranes were then washed twice in 2X SSPE and 0.05% SDS at 60° C. for fifteen minutes. Autoradiography was performed at −70° C. for 4–12 hours with enhancing screens.

4. Allele Specific Oligonucleotide Analysis

The $^{32}$P labeled ATP oligonucleotides hybridized to PCR products amplified from individuals possessing the 3888delGA mutation, and not to those from "normal" individuals. This hybridization was seen as exposed regions of the autoradiography film. Both positive (3888delGA) and negative (normal) controls were included in this analysis.

5. Result

Using the above PCR amplification and standard fluorescent sequencing technology, we have found a previously unidentified mutation in the BRCA1 gene. This mutation lies in segment "K" of exon 11. The DNA sequence results demonstrated a two base pair deletion containing nucleotides 3888 and 3889 of the published BRCA1 cDNA sequence. This mutation interrupts the normal reading frame of the BRCA1 transcript, resulting in the appearance of an in-frame terminator (TAG) at codon position 1265. This mutation is, therefore, predicted to result in a truncated, and most likely, non-functional protein. The formal name of the mutation will be 3888delGA.

Example 2

Diagnosis of individuals carrying the 3888delGA mutation.

Genomic DNA is isolated from white blood cells from a patient with a family history of breast or ovarian cancer. Section K of exon 11 of the BRCA1 gene is amplified from the genomic DNA using the polymerase chain reaction (PCR). The PCR primers used to amplify the suspected mutation are as follows:

SEQ ID NO: 3
```
BRCA1–11K–F: 5'-GCA AAA GCG TCC AGA AAG AG-3'
```
SEQ ID NO: 4
```
BRCA1–11K–R: 5'-AGT CTT CCA ATT CAC TGC AC-3'
```

1. PCR Amplification

The PCR amplification is carried out for approximately 35 cycles as described in EXAMPLE 1.

2. Dideoxy Sequence Analysis

PCR products are purified using QIA-QUICK® PCR purification kits (QIAGEN®, cat# 28104). Fluorescent dye is attached for automated sequencing using the TAQ DYE TERMINATOR® sequence terminator Kit (PERKIN-ELMER® cat# 401628). DNA sequencing is performed in accordance with the parameters specified in the TAQ DYE TERMINARTOR® Kit, in both forward and reverse directions, on an APPLIED BIOSYSTEMS, INC® (ABI) automated sequencer (Model 377).

3. Analysis

The software used for analysis of the resulting data was SEQUENCE NAVIGATOR® purchased through ABI.

4. Result

Using the above PCR amplification and standard fluorescent sequencing technology, a two base pair deletion containing nucleotides 3888 and 3889 of the published BRCA1 cDNA sequence can be found. This mutation interrupts the normal reading frame of the BRCA1 transcript, resulting in the appearance of an in-frame terminator (TAG) at codon position 1265. This mutation is, therefore, predicted to result in a truncated, and most likely, non-functional protein. A finding of this mutation may be used either to design a program of gene therapy in a patient having a tumor, to characterize a tumor, or as a prognostic tool for those at risk of developing breast or ovarian cancer Example 3

Detection of the 3888delGA Mutation by Hybridization

Genomic DNA is isolated from white blood cells from a patient with a family history of breast or ovarian cancer. Section K of exon 11 of the BRCA1 gene is amplified from the genomic DNA using the polymerase chain reaction (PCR). The PCR primers used to amplify the suspected mutation are as follows:

BRCA1–11K–F:
```
5'-GCA AAA GCG TCC AGA AAG AG-3' SEQ ID NO: 1
```

BRCA1–11K–R:
```
5'-AGT CTT CCA ATT CAC TGC AC-3' SEQ ID NO: 2
```

1. PCR Amplification

The PCR amplification is carried out for approximately 35 cycles as described in EXAMPLE 1. PCR products are purified using QIA-QUICK® PCR purification kits (QIAGEN®, cat# 28104). Fluorescent dye is attached for automated sequencing using the TAQ DYE TERMINATOR® sequence terminator Kit (PERKIN-ELMER® cat# 401628). DNA sequencing is performed in both forward and reverse directions on an APPLIED BIOSYSTEMS, INC® (ABI) automated sequencer (Model 377). The software used for analysis of the resulting data was SEQUENCE NAVIGATOR® analytical software purchased through ABI.

2. Detection of the 3888delGA mutation by Allele Specific Oligonucleotide Hybridization For rapid detection of the 3888delGA mutation, unlabeled PCR products from segment K of exon 11 can be blotted in duplicate onto a nylon membrane, air dried, and UV crosslinked. Hybridization is accomplished with $^{32}$P labeled ATP oligonucleotides corresponding to either the normal sequence

```
5'-GAA CAC AGA GGA GAA T-3', (SEQ. ID. NO. 5),
``` or

```
5'-TAA GAA CAC AGA GGA G-3', (SEQ. ID. NO. 6)
``` or with a sequence exhibiting the 3888delGA mutation such as

```
5'-GAA CAC AGG AGA AT-3' (SEQ ID NO: 3),
``` and
```
5'-TAA GAA CAC AGG AG-3' (SEQ ID NO: 4).
```

The membranes are then washed twice in 2X SSPE and 0.05% SDS at 60° C. for fifteen minutes. Autoradiography is performed at −70° C. for 4–12 hours with enhancing screens.

Although the invention has been described with reference to the presently preferred embodiments, it should be understood that various modifications can be made without departing from the spirit of the invention. Accordingly, the invention is limited only by the following claims.

We claim:

1. An isolated allele-specific oligonucleotide for use in detecting a two base pair deletion at nucleotides 3888 and 3889 in a BRCA 1 encoding target polynucleotide, wherein said allele specific nucleotide specifically hybridizes to said target polynucleotide at a location within said polynucleotide corresponding to said deletion and wherein said allele-specific oligonucleotide does not hybridize to a wild type BRCA1 sequence.

2. An isolated oligonucleotide according to claim 1 comprising the sequence: 5'-GAA CAC AGG AGA AT-3'(SEQ ID NO. 3).

3. An isolated oligonucleotide according to claim 2 which is labeled with a radiolabel, a fluorescent label, a bioluminescent label, a chemiluminescent label, or an enzyme label.

4. An isolated oligonucleotide according to claim 1 comprising the sequence. 5'-TAA GAA CAC AGG AG -3'(SEQ ID NO. 4).

5. An isolated oligonucleotide according to claim 4 which is labeled with a radiolabel, a fluorescent label, a bioluminescent label, a chemiluminescent label, or an enzyme label.

6. An isolated allele-specific oligonucleotide primer for amplifying a region of a BRCA1 encoding target polynucleotide, which is a forward primer comprising the sequence: 5'-GCA AAA GCG TCC AGA AAG AG-3'(SEQ ID NO 1), wherein said primer specifically hybridizes to said target polynucleotide, and thereby permits the amplification of a portion of said target polynucleotide that includes nucleotides 3888 and 3889 of a BRCA1 cDNA having the nucleotide sequence of GenBank Accession Number U14680.

7. The isolated oligonucleotide primer of claim 6 which is labeled with a radiolabel, a fluorescent label, a bioluminescent label, a chemiluminescent label, or an enzyme label.

8. An isolated oligonucleotide primer according to claim 6 which is a reverse primer comprising the sequence: 5'-AGT CTT CCA ATT CAC TGC AC-3 (SEQ ID NO 2).

9. An isolated oligonucleotide primer according to claim 8 which is labeled with a radiolabel, a fluorescent label, a bioluminescent label, a chemiluminescent label, or an enzyme label.

10. A method of detecting a genetic predisposition to breast and ovarian cancer in an individual by detecting a two base pair deletion at nucleotides 3888 and 3889 of a BRCA1 encoding target polynucleotide comprising:

a) obtaining a sample comprising BRCA1 encoding polynucleotides from an individual;

b) hybridizing said polynucleotides to the allele-specific oligonucleotide of claim 1 under hybridization conditions wherein a hybrid will form between said allele-specific oligonucleotide and a BRCA1 encoding polynucleotide which comprises a two base pair deletion at nucleotides 3888 and 3889 of a BRCA1 encoding target polynucleotide, and will not form between a BRCA1 encoding polynucleotide that does not contain said two base pair deletion;

c) detecting any hybrids formed and correlating the presence of hybrids formed with a genetic predisposition to breast and ovarian cancer.

11. A method according to claim 10 further comprising amplifying a fragment of BRCA1 nucleic acids wherein said fragment comprises a sequence which is a portion of the BRCA1 gene including said two base deletion or wherein said fragment comprises a sequence which is a portion of the BRCA1 gene including nucleotides 3888 and 3889.

12. A method according to claim 11 wherein said fragment is amplified with an oligonucleotide primer having a sequence comprising a) 5'GCA AAA GCG TCC AGA AAG AG-3' (SEQ ID NO: 1), or b) 5'-AGT CTT CCA ATT CAC TGC AC 3' (SEQ ID NO: 2).

13. A method according to claim 10 wherein said allele-specific oligonucleotide is labeled with a radiolabel, a fluorescent label, a bioluminescent label, a chemiluminescent label, or an enzyme label.

14. A method of detecting a genetic predisposition to breast and ovarian cancer in an individual by detecting a two base pair deletion at nucleotides 3888 and 3889 of a BRCA1 encoding target polynucleotide, comprising:

a) digesting DNA comprising BRCA1 encoding polynucleotides from said individual with a restriction endonuclease;

b) separating DNA fragments obtained from said digestion by gel electrophoresis and immobilizing said fragments on a membrane by Southern blotting;

c) hybridizing said immobilized fragments to the allele-specific oligonucleotide of claim 1 under hybridization conditions wherein a hybrid will form between said allele specific oligonucleotide and a fragment of a BRCA1 encoding polynucleotide which comprises a two base pair deletion at nucleotides 3888 and 3889 of said BRCA1 encoding target polynucleotide, and will not form between a fragment of a BRCA1 encoding polynucleotide that does not contain said two base pair deletion;

c) detecting any hybrids formed and correlating the presence of hybrids formed with a genetic predisposition to breast and ovarian cancer.

15. A method according to claim 14 wherein said allele specific oligonucleotide comprises:

(a) 5'-GAA CAC AGG AGA AT-3'(SEQ ID NO 3), or (b) 5'-TAA GAA CAC AGG AG-3'(SEQ ID NO. 4).

16. A method according to claim 14 wherein the allele specific oligonucleotide is labeled with a radiolabel, a fluorescent label, a bioluminescent label, a chemiluminescent label, or an enzyme label.

17. The method of claim 12 or 14 wherein said oligonucleotide primer is labeled with a radiolabel, a fluorescent label, a bioluminescent label, or an enzyme label.

* * * * *